United States Patent [19]

Michaels et al.

[11] 4,177,256

[45] Dec. 4, 1979

[54] OSMOTIC BURSTING DRUG DELIVERY DEVICE

[75] Inventors: Alan S. Michaels, San Francisco, Calif.; Mark S. Guillod, Kaneohe, Hi.

[73] Assignee: ALZA Corporation, Palo Alto, Calif.

[21] Appl. No.: 855,605

[22] Filed: Nov. 29, 1977

Related U.S. Application Data

[63] Continuation-in-part of Ser. No. 578,979, May 19, 1975, abandoned, which is a continuation-in-part of Ser. No. 465,276, Apr. 29, 1974, abandoned, which is a continuation-in-part of Ser. No. 354,359, Apr. 25, 1973, abandoned.

[51] Int. Cl.² .................. A61K 9/22; A61K 9/26; A61K 9/52; A61K 9/54
[52] U.S. Cl. ............................ 424/22; 424/19; 424/20; 128/260
[58] Field of Search ............ 128/260; 424/141.6, 424/19–22, 32–33, 78–83

[56] References Cited

U.S. PATENT DOCUMENTS

| | | | |
|---|---|---|---|
| 2,478,182 | 8/1949 | Consolazio | 424/22 X |
| 3,376,238 | 4/1968 | Gregorian et al. | 260/2.5 |
| 3,618,604 | 11/1971 | Ness | 128/260 |
| 3,710,795 | 1/1973 | Higuchi et al. | 128/260 |
| 3,732,865 | 5/1973 | Higuchi et al. | 128/260 |
| 3,760,805 | 9/1973 | Higuchi | 128/260 |
| 3,760,806 | 9/1973 | Leeper | 128/260 |
| 3,760,984 | 9/1973 | Theeuwes | 222/45 |
| 3,811,444 | 5/1974 | Heller et al. | 128/260 |
| 3,828,777 | 8/1974 | Ness | 128/260 |
| 3,845,770 | 11/1974 | Theeuwes et al. | 128/260 |
| 3,854,480 | 12/1974 | Zaffaroni | 128/260 |
| 3,867,519 | 2/1975 | Michaels | 424/19 |
| 3,903,880 | 9/1975 | Higuchi et al. | 128/130 |
| 3,923,939 | 12/1975 | Baker et al. | 264/49 |
| 3,952,741 | 4/1976 | Baker | 128/260 |
| 3,991,759 | 11/1976 | Urquhart | 128/260 |
| 4,052,505 | 10/1977 | Higuchi et al. | 424/14 |
| 4,057,619 | 11/1977 | Higuchi et al. | 424/14 |
| 4,069,307 | 1/1978 | Higuchi et al. | 424/22 |

OTHER PUBLICATIONS

Ellis and Smith Handbook of Ocular Therapeutics and Pharmacology, 3rd Ed. 1969, C. V. Mosby, St. Louis, Mo., pp. 171, 172, 192, 193.

Physician's Desk Reference for Ophthalmology 1976/1977 ed. p. 85, Medical Economics Co., Oradell, N.J.

Narkis et al., J. Applied Polymer Sci., 20:3431-3436 (1976), "Slow Release of Water-Soluble Salts from Polymers".

Marson J. Appl. Chem., 1969, vol. 19, Apr., pp. 93–99, Antifouling Paints, "I. Theoretical Approach to Leaching of Soluble Pigments from Insoluble Paint Vehicles".

*Primary Examiner*—Shep K. Rose
*Attorney, Agent, or Firm*—Thomas E. Ciotti; Paul L. Sabatine; Edward L. Mandell

[57] ABSTRACT

A drug delivery for administering drug to an aqueous body environment at a substantially constant rate. The devices consist essentially of a mixture of drug of specific average particle size dispersed in a polymer of specific water permeability, tensile strength, and Young's modulus in specific volume proportions such that the particles are surrounded substantially individually by the polymer. The constancy of the release rate of drug from the devices is governed by the drug particle size and volume proportion of drug in the mixture.

12 Claims, 17 Drawing Figures

TIMES 1205

FIG.5

TIMES 242

OSMOTIC BURSTING DRUG DELIVERY DEVICE

CROSS-REFERENCE TO RELATED APPLICATIONS

This application is a continuation-in-part of application Ser. No. 578,979 filed May 19, 1975, now abandoned which in turn is a continuation-in-part of application Ser. No. 465,276 filed Apr. 29, 1974 and now abandoned, which in turn is a continuation-in-part of application Ser. No. 354,359 filed Apr. 25, 1973 and now abandoned.

BACKGROUND OF THE INVENTION

1. Field of the Invention

The present invention relates to a novel device which is useful for releasing drug into aqueous environments of the body. More particularly, the invention relates to a new sustained release delivery device for drugs which enables the release of drugs at a substantially constant rate over a prolonged period of time.

2. Description of the Prior Art

Many sustained release formulations of drug and polymer are described in the medical art literature. Most of these formulations release their drug by either (1) diffusion, in which the drug diffuses through the polymer or the polymer swells with body fluid and the drug is leached from the polymer by such fluid, or (2) erosion, in which the polymer disintegrates or dissolves in body fluids to release entrapped drug. The release of drug from the present invention is not governed by such diffusion or such erosion.

Controlled release drug delivery systems that operate as osmotically driven pumps are also known. For instance, U.S. Pat. No. 3,916,898 describes a system that consists of an osmotically effective drug core encapsulated by a drug impermeable, water permeable coating. The coating has one or more specifically sized outlets in it. The core may consist of a mixture of a drug, such as pilocarpine nitrate, and a polymer binder, such as ethylene-vinyl acetate copolymer. Initially water permeates through the coating to dissolve part of the drug core. Additional water is then imbibed by the core to generate hydrostatic pressure within the core that causes the drug solution to be pumped out through the outlet port(s) in the coating. In contrast the devices of the present invention do not include a coating with defined outlet ports. Instead the present devices consist of a mixture of drug of specific particle size and polymer in specific volume proportions. The parameters governing the release rate of drug from these devices are different than those governing the release rate from the osmotically driven pumps.

U.S. Pat. No. 3,427,066 describes medicinal beads that release drug by a bursting mechanism. The beads consist of a core of water-swellable colloid containing a drug and a thin coating of polymer that is inert to gastrointestinal fluids and permeable to water. When the beads are ingested, water diffuses inwardly through the polymer coating causing the colloid core to swell. This swelling creates sufficient pressure to burst the polymer coating, thereby releasing the entire quantity of drug in the core. The present invention releases drug by a bursting mechanism but not one that involves beads that have a water-swellable colloid core.

U.S. Pat. No. 2,478,182 describes salt tablets in the form of a tablet of compressed salt granules coated with cellulose nitrate of acetate. According to the patent the cellulose derivative penetrates the tablet and forms a honeycomb structure around the compressed granules. Upon ingestion water dialyzes into the compartments of the honeycomb and salt dialyzes out. When the compartments become engorged with water, the compartments burst and liberate salt. The tablets are exhausted in 60–80 minutes. In comparison the devices of the invention provide truly sustained release at a substantially constant rate. The proportion of polymer in the invention devices is grossly larger than that of the salt tablets. Also, the particle size of the sale granules is not in accord with the drug particle specifications of the invention.

The agricultural chemical art literature describes various slow release formulations of fertilizer or pesticide and polymer. Numerous agricultural chemical art references are cited in the files of the above-mentioned cross-reference parent U.S. patent applications. Those references are generally concerned with achieving only slow release of a chemical and are not concerned with the controlled, precise release associated with the present invention. None of these references suggest that chemical is released by a bursting mechanism and the few that mention a release mechanism at all indicate that release occurs via diffusion or erosion similar to that described above.

"Anti-Fouling Paints", Masson, F., *J. Applied Chem.*, Vol. 19, pages 93–99, April 1969, an article totally unrelated to the medical art, describes a mechanism similar to the bursting mechanism by which the present invention releases drug. This article relates to "contact-leaching" marine paints, that is, paints that contain enough pigment for direct contact to occur between adjacent pigment particles in the paint vehicle, such that as one pigment particle is dissolved by the leachate, the adjacent one is exposed to the leachate. It is specifically concerned with explaining the deviation between the actual leaching kinetics and the theoretical leaching kinetics of such paints. A mathematical paint model is proposed consisting of a single, soluble pigment in a stable, insoluble resin vehicle, with the individual pigment particles wet completely by the vehicle. In a layer of such paint, the pigment particles are postulated to be encased in a thin film of resin that exhibits brittle fracture under stress. It is postulated that (a) as one particle is leached from the layer, the thin film of resin that separates it from the adjoining particle is exposed to the leachate, (b) the leachate diffuses through the resin film and dissolves some of the adjoining pigment particle, (c) the resulting osmotic pressure ruptures the film, and (d) the solvated pigment diffuses out through the thus formed interconnecting holes in the layer. This article is believed to be irrelevant to the present invention because it is in an unrelated art and is not concerned with dispensing materials but rather with explaining the leaching kinetics of marine paints.

SUMMARY OF THE INVENTION

The invention is a drug delivery device for administering drug continuously to an aqueous body environment for a prolonged time period at a controlled rate. The device is in the form of a solid, unit body that is sized and shaped for placement in the environment and is made at least in part of a mixture that defines a surface of predetermined area that is exposed to the water of the environment, and constitutes a substantial portion of the surface area of the device that is exposed to the water of the environment, said mixture being comprised of about 15% to about 90%, by weight, of discrete depots 0.1 to 250 microns, surface area average diameter, in size of a drug composition that is an osmotically effective solute, the depots being dispersed in about 10% to about 85%, by weight, of a polymer such that the depots are surrounded substantially individually by a layer of polymer, the polymer being substantially impermeable to the drug composition, insoluble in the environment at least during the prolonged time period, and permeable to water, and having a tensile strength, a Young's modulus, and maximum elongation such that the cohesive strength of said layer is exceeded by the pressure that the depot the layer surrounds is able to generate by imbibing water. When the device is placed in the environment, water is imbibed by the depots in a serially inwardly manner beginning with the depots at or nearest said surface, and said pressure is generated therein causing the polymer layers surrounding those depots to rupture thereby releasing the drug composition therefrom to the environment.

Preferred embodiments of the invention release drug at a substantially constant rate. Such embodiments are in the form of a solid unit body that is sized and shaped for placement in the environment and consists essentially of a mixture of (i) about 1% to about 50% by volume of a drug composition that when in aqueous solution exhibits an osmotic pressure of at least about 10 atmospheres and that is in the form of discrete depots having a surface area average diameter, d, of about 0.1 to about 250 microns, with the proviso that:

$$d \geq \frac{0.5}{\left(\frac{\pi}{.06\Phi}\right)^{\frac{1}{3}} - 1} \quad (1)$$

wherein $\Phi$ is the volume percent of drug composition in the mixture and (ii) about 50% to about 99% by volume of a polymer that has a permeability to water at ambient temperature of about $10^{-8}$ to about $10^{-12}$ g cm/cm² sec cm Hg, a tensile strength of about 200 to about 3000 psi a Young's modulus of about 200 to about 3000 psi and is substantially impermeable to the drug composition and insoluble in the environment at least during the prolonged time period; the depots being dispersed in the polymer such that the depots are surrounded substantially individually by the polymer. When placed in an aqueous body environment these preferred embodiment release the drug composition to the environment at a rate proportional to:

$$\frac{\rho \Phi \times 10^{-2} k \Delta \pi A}{d(\lambda^3 - 1)\left[1 - \left(\frac{.06\Phi}{\pi}\right)^{\frac{1}{3}}\right]} \quad (2)$$

where $\rho$ is the density of the drug composition and is in the range of about 0.5 to about 8 g/cm³, k is said permeability to water, A is the surface area of the device that is exposed to the environment, $\Delta\pi$ is the difference between said osmotic pressure and the osmotic pressure of the environment, d and $\Phi$ are as defined above, and $$\lambda^2 - \lambda^{-4} = (3T_s/Y) \quad (3)$$

wherein $T_s$ is said tensile strength and Y is said Young's modulus, with the proviso that $\lambda$ is in the range of 1.02 and 4.0.

BRIEF DESCRIPTION OF THE DRAWINGS

In the description of the invention which follows, references will be made to the accompanying drawings wherein.

Whenever possible, like numbers are used to designate like parts in these Figures.

DETAILED DESCRIPTION OF THE INVENTION

Figure 1:
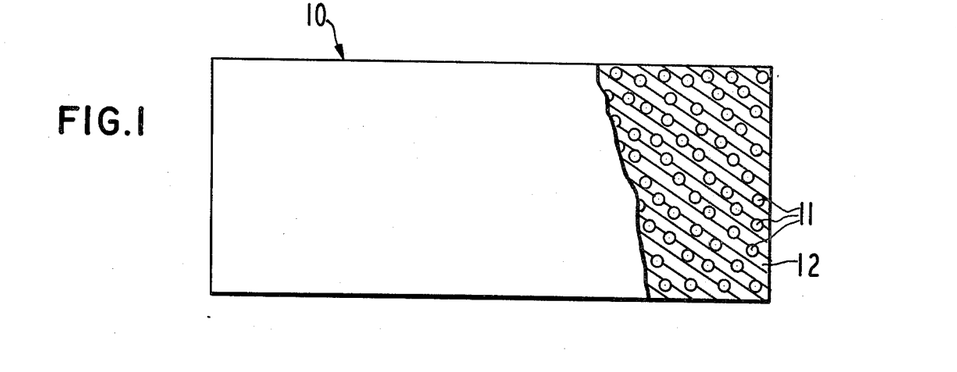
FIG. 1 is an enlarged cross-sectional view of a delivery device of this invention.

FIG. 1 depicts one of the more basic embodiments of the invention, namely a drug delivery device 10. Device 10 comprises a plurality of discrete depots 11 of drug composition dispersed through a polymer matrix 12. The polymer of matrix 12 surrounds and encloses the depots 11 and binds them into a solid, unit body. Ideally matrix 12 surrounds depots 11 individually so that each depot 11 is encapsulated by a layer of polymer and is separated from adjacent depots by at least about 0.5 microns. In practice, it is impossible to achieve such ideal dispersion with a large number of depots and there will be some degree of agglomeration of and/or contact between depots within the matrix 12. The phrase "surrounded substantially individually" as used herein is intended to indicate such deviation from the ideal.

The drug composition that forms depots 11 and the polymer that forms matrix 12 meet the specifications stated above. Similarly, the proportion of depots 11 in device 10, is as specified above. The drug composition of depots 11 may be composed of either neat drug that exhibits the specified osmotic pressure, a drug that exhibits insignificant osmotic pressure mixed with a compound that exhibits the specified osmotic pressure, or a drug mixed with one or more compounds that combined exhibit the specified osmotic pressure.

Matrix 12 initially is essentially imperforate so that when device 10 is placed into the body environment no drug composition, except for that located at the surface of device 10 exposed to the environment, is lost by simple dissolution (leaching). And since the polymer forming matrix 12 is substantially impermeable to the drug composition there is substantially no release of drug composition from device 10 by diffusion through the dense polymer.

Figure 2:
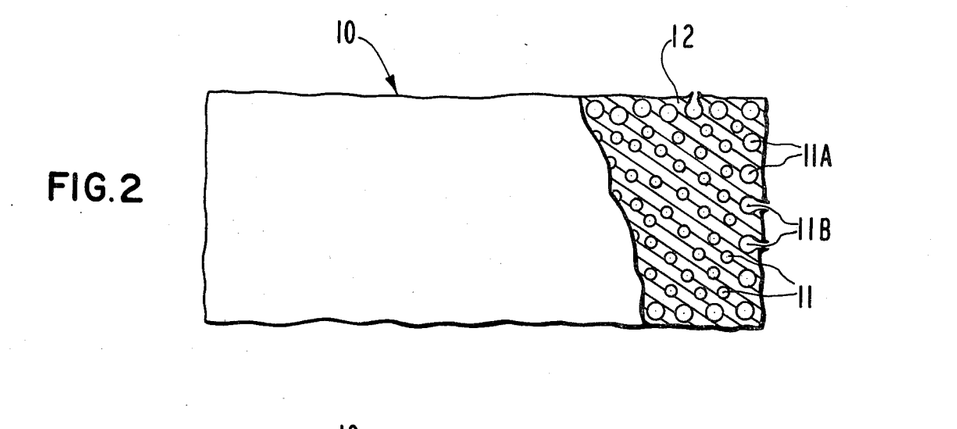
FIGS. 2 and 3 are enlarged cross-sectional views of the device of FIG. 1 after two different periods of use.

When device 10 is placed in the environment water permeates through the water permeable polymer forming matrix 12 into the outermost depots (designated 11A in FIG. 2) to dissolve drug composition thereof. The osmotic pressure exhibited by the resulting solution of drug composition in the outermost depots creates an osmotic pressure gradient between the same and the body fluid of the environment. This gradient causes water to be imbibed from the environment into the outermost depots and hydrostatic pressure to be generated therein. FIG. 2 depicts device 10 shortly after it has been placed in a body environment. As shown in FIG. 2 at first only the outermost depots 11A imbibe water instead of all the depots imbibing water equally. When the hydrostatic pressure in a depot exceeds the cohesive strength of the polymer layer surrounding the depot, the layer ruptures, releasing the drug composition contained therein to the environment, as illustrated by ruptured depots 11B. Such rupture causes the depot contents to be released to the environment. After a significant portion of the depot's contents have been so released water begins permeating from the depot inwardly through the polymer to the next innermore depot, and the solution-imbibition-rupture-release sequence described above occurs with respect thereto. This sequence continually repeats itself resulting in a serially inward bursting of depots until the innermost depots eventually are exposed to water and burst.

Figure 3:
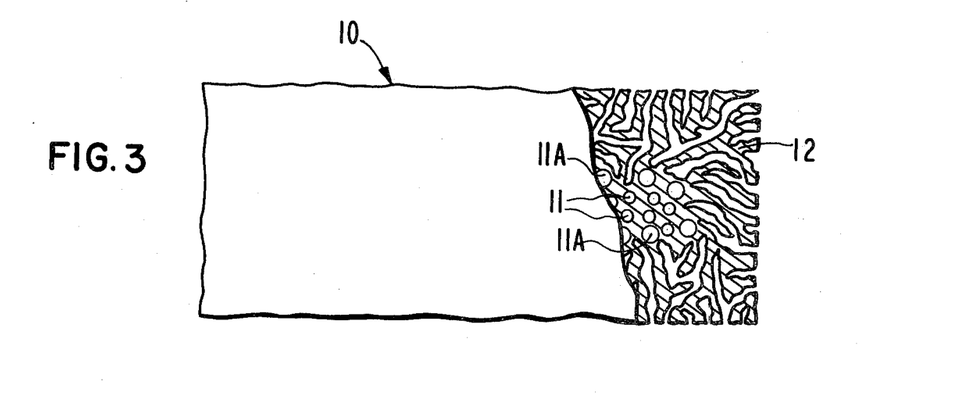

As shown in FIG. 3 the release of drug composition from device 10 transforms that portion of the device from which the release has occurred into a polymeric lattice. The lattice structure of the exhausted portion of the device is exaggerated in FIG. 3 for the purpose of illustration. Depending upon the elastomeric properties of the polymer forming the matrix, the polymer may relax or retract after such rupture causing the lattice structure to be indiscernible.

It is essential that device 10 include a substantial number of depots if continuous release at a substantially constant rate is to be realized. If there was only one depot, for instance, its uncontrolled rupture would cause the instantaneous pulse release of the entire contents of the single depot. Then number of depots is a function of the depot loading and the size of the depots. Depot size affects the kinetics of drug release from the device and is important as regards the constancy of the release rate and the precision of the release rate. Constancy is an important factor in the quality and effectiveness of many therapies and precision is important as regards facilitating quality control and meeting label representations. Functionally, the depots must not be so small as to (1) inhibit them from being dispersed uniformly in the polymer with a high degree of discreteness, that is, a high degree of individual encapsulation by the polymer, or (2) adversely affect their ability to imbibe sufficient water to burst the surrounding polymer skin. Correlatively, the depots must not be so large as to (1) inhibit them from being dispersed uniformly in the polymer, or (2) make the release rate of drug from the device depend significantly on the rate of dissolution of the drug composition.

As indicated above, the release rate of drug from the preferred embodiments of the invention is proportional to relationship 2 above. Three of the parameters of that relationship, $\rho$, $\pi$, and d, concern inherent properties of the drug composition. The osmotic pressure of the drug composition, $\pi$, depends on the solubility of the drug composition in water and the number of solute species the drug composition creates in solution. The surface area average diameter, d, of the depots may be calculated from measurements of the specific surface area of the composition. Such measurements may be made according to the procedures described in the following references. S. Brunauer, P. Emmett, E. Teller, J. Am. Chem. Soc. 60, 309 (1938); S. Gregg, "The Surface Chemistry of Solids", 2nd ed., Reinhold Publishing Corp., N.Y. (1961); S. Gregg and K. Sing, "Adsorption, Surface Area and Porosity", Academic Press, N.Y. (1967); D. Yound and A. Crowell, "Physical Adsorption of Gases", Butterworth and Co. Ltd., London (1962); C. Orr and J. M. Dalla Valla, "Fine Particle Measurements", Macmillan, N.Y. (1959).

The relationship between the specific surface area and the surface area average diameter, d, in microns has been determined to be:

$$d = 6/\rho A_s \qquad (4)$$

wherein $\rho$ is as defined previously and is in g/cm³ and $A_s$ is the specific surface area of the drug composition in m²/g. It will be appreciated that said specific surface area measurements provide integrated values and that d is thus an average value. Also equation 4 assumes the depots exist as nonporous spheres, and is accordingly an approximation in this respect. Likewise three of the parameters k, $T_s$ and Y ($T_s$ and Y define $\lambda$) are inherent properties of the polymer that forms matrix 12. Each of these parameters is measurable by known techniques. The remaining parameters, A and $\Phi$, concern, respectively, the geometry and composition of device 10.

The parameters d and $\Phi$ have been found to significantly affect the constancy and precision of the release rate of drug composition from the preferred embodiments. As indicated by relationship 1 above these parameters have interrelated effects on the release rate. When relationship 1 is satisfied and d and $\Phi$ fall within the ranges specified above, the release rate of drug composition from the device is substantially constant. That is, the standard deviation in the release rate is no greater than 15% over the period between 20% and 80%, inclusive, cumulative drug release as determined by ten measurements of the release rate taken at equispaced intervals over that period. Otherwise the release rate will be approximately proportional to time$^{-\frac{1}{2}}$.

In particularly preferred embodiments of the invention $\pi$ is 10 to 2000 atm, d is 1 to 50 microns, $\Phi$ is 5% to 35%, the volume percent of polymer is 65% to 95%, k is $10^{-9}$ to $10^{-10}$ gcm/cm² sec cm Hg, $T_s$ is 400 to 1500 psi, Y is 300 to 1500 psi, and the polymer has a maximum elongation of 200% to 1700%.

Polymeric materials for forming the matrix 12 include materials known to the art for making osmosis and reverse osmosis membranes, such as commercially available cellulose acetate and its derivatives, partial and completely hydrolyzed ethylene-vinyl acetate copolymers, highly plasticized polyvinyl chloride, homo- and copolymers of polyvinyl acetate, polyesters of acrylic acid and methacrylic acid, polyvinyl alkyl ethers, polyvinyl fluoride, silicone polycarbonates, aromatic nitrogen-containing polymeric membranes that exhibit water permeability and essentially no solute passage, osmosis membranes made from polymeric epoxides, osmosis membranes made from copolymers of an alkylene oxide and alkyl glycidyl ether, semipermeable polyurethanes, semipermeable polyglycolic or polylactic acid and derivatives thereof, the membranes of ionically associated polyelectrolytes, the polymers formed by the coprecipitation of polycation and polyanion as described in U.S. Pat. Nos. 3,276,586, 3,541,005, 3,541,006, 3,546,142 and 3,173,876, derivatives of polystyrene such as poly(sodium styrenesulfonate) and poly(vinylbenzyltrimethyl-ammonium chloride), and the like. Ethylene-vinyl acetate copolymers, are preferred. It should be understood that the polymer, regardless of its chemical structure, must meet the previously stated specifications to be useful in the invention.

The term "drug" as used herein encompasses any chemical compound or biological agent which may be administered to a patient to aid in the diagnosis, treatment or prevention of disease or to control or improve any pathological or physiological condition. "Drugs" include, without limitation, hypnotics, sedatives, psychic energizers, tranquilizers, anti-convulsants, muscle relaxants, analgesics, anti-inflammatory agents, anesthetics, anti-spasmodics, anti-ulcer agents, anti-microbials, cardiovascular agents, diuretics, anti-neoplastic agents, anti-viral agents, anti-glaucoma agents, and the like. The drug can be in various forms, such as uncharged molecules, components of molecular complexes, pharmacologically acceptable salts such as hydrochloride, hydrobromide, sulfate, phosphate, citrate, nitrate, borate, acetate, maleate, tartrate, salicylate, and the like. For acidic drugs, salts of metals, amines or organic cations, for example quaternary ammonium can be employed.

As noted, the water solubility of the drug is important as regards the drug's ability to generate the specified osmotic pressure in solution. Drugs having a solubility in water of at least 1% by weight usually have such ability. Typical water-soluble drugs include, without limitation, ephedrine hydrochloride, ephedrine sulfate, hydroxy-amphetamine, isoproterenol hydrochloride, cholinecarbamyl chloride, pilocarpine hydrochloride, pilocarpine nitrate, demecarium bromide, echothiophate iodide, physostigmine salicylate, propranolol hydrochloride, homatropine hydrochloride, homatropine methylbromide, methscopolamine nitrate, alverine citrate, chlorophenoxamine hydrochloride, calcium pantotheate, epinephrine bitartrate, chloramphenicol sodium succinate, hydrocortisone phosphate, hydrocortisone sodium succinate, gentamicin sulfate, neomycin sulfate, prednisolone sodium phosphate, tetracycline hydrochloride, polymixin sulfate and the like.

Limited solubility drugs, that is drugs that have a solubility in water of less than 1% by weight, normally are not capable of generating the required osmotic pressure and thus a compound having such a capability must be added to the drug. Even with water-soluble drugs, the addition of such compounds may enable a more precise control of the pressure gradient that is generated, and hence more precise control of the drug release rate. These added compounds are normally essentially pharmacologically inert and include water-soluble inorganic and organic salts and carbohydrates such as magnesium sulfate, magnesium chloride, sodium chloride, lithium chloride, potassium sulfate, sodium carbonate, sodium sulfite, lithium sulfate, calcium bicarbonate, sodium sulfate, calcium sulfate, potassium acid phosphate, calcium lactate, magnesium succinate, tartaric acid, acetamide, choline chloride, soluble carbohydrate such as sorbitol, mannitol, raffinose, glucose, sucrose, lactose, mixtures thereof and the like. Limited solubility drugs which may be delivered by the use of such added solutes include hormones, such as estrogenic and progestational hormones; steroids, such as hydrocortisone alcohol or acetate and prednisolone acetate; and other drugs such as bacitricin, idoxuridine, and clonidine HCl.

Common additives such as pigments, stabilizers antioxidants, surfactants, and binders may be included in the polymer-drug composition depot mixture. However, such additives, in kind and amount, should not affect the basic and novel characteristics of the device. The same may be said for the inclusion of elements other than the mixture in the overall make-up of the device.

Delivery device 10 offers many advantages over conventional drug forms. It provides, in a single device needing only one application, a quantity of drug sufficient for an entire therapeutic regimen. This large quantity of drug may be safely administered at one time without fear of accidental total release by puncture of the device. The device is simple and of potentially inexpensive construction. Importantly, the device may be used in any water-containing patient body environment irrespective of the environment's pH, enzyme activity, or fluid turnover rate. With the erosion and diffusion devices of the prior art, changes in environment conditions, such as a change in the environment's pH as might occur if a device were to pass through the gastrointestinal tract, would effect major changes in the device's release characteristics.

Also, the devices of this invention permit drug release to be continued over prolonged periods of time. Rate of delivery can be adjusted by varying one or more of the parameters of relationship 2 above. The time period over which drug is released may vary widely depending upon the desired therapy. Normally the drug will be released for at least two hours. Ocular insert embodiments of the device will usually release drug for at least ½ day, often for up to two weeks. Intrauterine device embodiments for contraception purposes will release drug for months. Thus, the term "prolonged time period" means a period of at least two hours and connotes for a given device the time period over which release is required to achieve the desired therapy.

The present invention potentially finds application in the release of all drugs to all aqueous body environments of a patient. Although not expressly defined hereinbefore, it should be clear that an aqueous body environment can be any body tissue or body cavity, internal or external, which contains an aqueous medium. Typical aqueous body environments include the sacs of the eye, the gastrointestinal tract, the vagina or uterus, muscle tissue or the circulatory system. Devices of this invention may assume a wide variety of shapes, sizes and configurations for insertion, placement and implantation in or administration to these different aqueous body environments as are known in the art.

Figure 6:
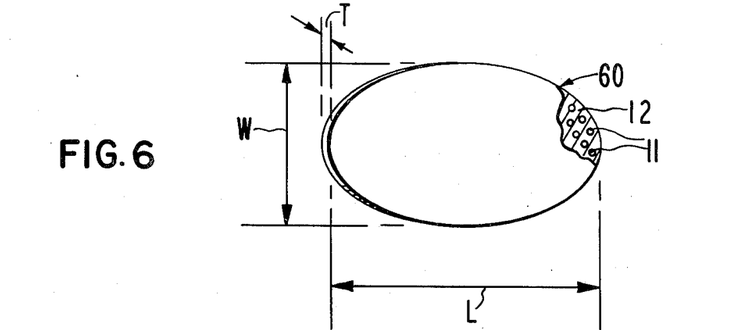
FIG. 6 is a partially cut-away enlarged perspective view of an elliptical embodiment of the invention for releasing drugs to the eye.

In one preferred embodiment, the device is in the form of a drug-dispensing ocular insert. A typical ocular insert is shown in FIG. 6 as device 60. Device 60 is illustrated in an elliptical configuration and in an enlarged size. In practice, device 60 would be of a size adapted for insertion and retention in the upper or lower cul-de-sac of the eye, say 6–25 mm long by 4–10 mm wide by 0.1–2 mm thick, and also might assume any shape conducive to such insertion and retention. Such placements are illustrated schematically in FIG. 7.

Figure 7:
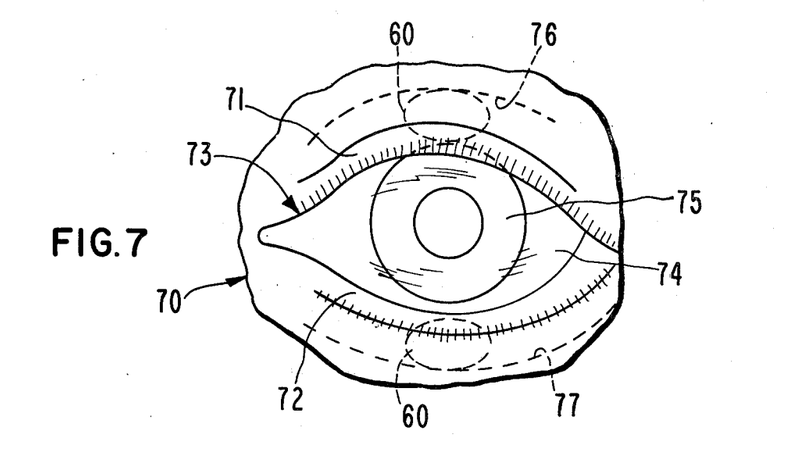
FIG. 7 is an elevational view of an eye illustrating the use of the devices of FIG. 6.

In FIG. 7, two elliptical ocular device 60 of this invention are depicted positioned for administering drug to eye 70. Eye 70 is comprised of an upper eyelid 71 and a lower eyelid 72, and eyeball 73 covered for the greater part of its posterior area by a sclera 74 and at its central area by a cornea 75. Eyelids 71 and 72 are lined with an epithelial membrane or palpebral conjunctiva, not shown, and sclera 74 is lined with a bulbar conjunctiva which covers the exposed surface of eyeball 73. Cornea 75 is covered with a transparent epithelial membrane, not shown in this figure. The portion of the palpebral conjuctiva which lines upper eyelid 71 and the underlying portion of the bulbar conjunctiva defines an upper cul-de-sac, shown by dotted line 76, while that portion of the palpebral conjunctiva which lines lower eyelid 72 and the underlying portion of the bulbar conjunctiva defines a lower cul-de-sac, shown by dotted line 77 in FIG. 7. The novel drug delivery device 60 of this invention is designed for insertion into cul-de-sac 76 of the conjunctiva between sclera 74 of eyeball 73 and upper eyelid 71 or in cul-de-sac 77 of the conjunctiva between the sclera 74 of eyeball 73 and lower eyelid 72, generally to be held in the drug administration position by the natural pressure of the respective eyelid. Device 60 comprises a water-permeable matrix 12 having dispersed throughout a plurality of discrete depots 11 of a suitable drug composition. The ocular sacs provide a suitable aqueous environment for device 60 to operate in. The tear fluids present in the ocular sacs contain water which is imbibed through matrix 12 into the outermost depots by osmosis, generating pressure within those depots. This pressure eventually bursts the outer depots' enclosing polymer matrix, frees the depots' drug and gives the tear fluids access to underlying depots and so forth. The external result of such serial bursting of the depots is a sustained continuous delivery of drug to the eye.

As indicated above, the shape and size of a delivery device are factors which play a part in the rate at which drug is released from the device. The water imbibition-bursting release mechanism, as has been described, involves drug release from an inward-migrating bursting surface or front. The rate or release is a function of the area of this surface or front. A drug delivery device of the configuration of device 60, by its relative thinness, is essentially a two-dimensional device. Thus, as it releases drug it will present a substantially constant surface area. Assuming that the distribution of depots 11 through the matrix 12 is uniform, this constant surface area should result in a relatively uniform rate of drug release.

Because of the small distance (thickness) through which the bursting front travels during use of a device like device 60, the rate of front travel must be very low, especially when the delivery is substantially prolonged. Such a slow-moving front potentially is unduly subject to disturbance. A configuration of the device of this invention which leads to the presentation of a uniform area for bursting without the potential disadvantages of the device of FIG. 6, is device 80 of FIG. 8. Device 80 comprises a core 81 having a portion of its surface exposed and the remainder of its surface covered with a membrane or coating 82. Core 81 is made up of a plurality of depots 11 dispersed in and enclosed by matrix 12. Depots 11 and matrix 12 act in concert to deliver drug through the exposed area of core 81 by the bursting mechanism described with reference to FIGS. 1, 2 and 3. Membrane or coating 82 is a material substantially impermeable to passage of the drug composition of depots 11 but also impermeable to water. With device 80, the water diffuses into the core substantially through the two exposed ends of the device, and the bursting occurs at two fronts which move from the exposed ends inwardly. The area of the bursting fronts remains essentially constant as they move through device 80. Device 80 is simple to fabricate. A long tube of membrane or coating 82 filled with core 81 can be extruded and cut into suitable lengths.

Figure 9:
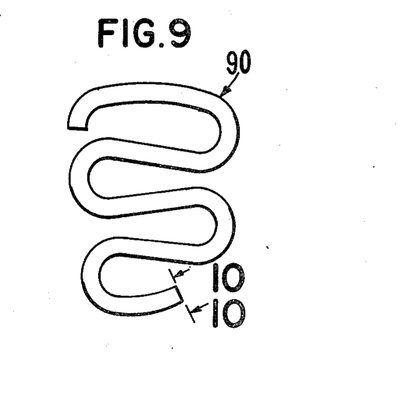
FIGS. 9 and 11 are enlarged elevational views of two devices embodying the invention for releasing drugs intrauterinely.
Figure 10:
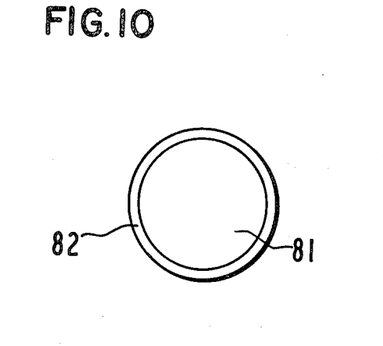
FIG. 10 is an end view of the exposed end of the devices of FIGS. 9 and 11.
Figure 11:
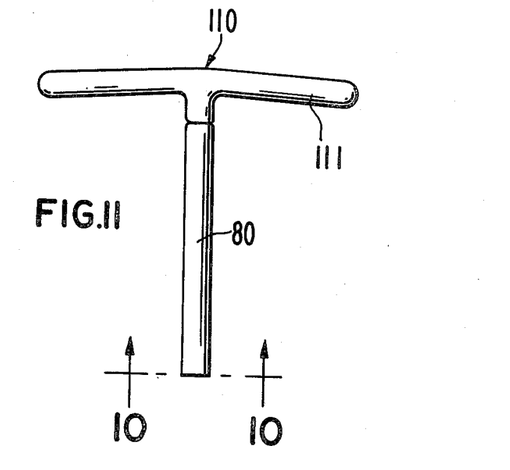

Another embodiment of the device of this invention is a drug dispensing intrauterine device. FIGS. 9 and 11 illustrate devices of this invention in two of the many art-recognized forms which a uterine retentive device may assume. Device 90 of FIG. 9 is a loop-shaped device of a shape and size suited for insertion through the cervix into the uterus. Device 110 of FIG. 11 is a "T"-shaped device also of a shape and size suited for uterine placement. Device 90 has a structure similar to that of device 80. As shown in FIG. 10, device 90 comprises a core 81 having bonded thereto outer covering 82. Core 81 comprises a polymer matrix containing drug depots in accord with this invention. These details are not shown in FIG. 10. Covering 82 is impermeable to the drug composition of the depots and to the aqueous uterine fluid. Water diffuses into core 81 through the two exposed ends, causing the depots to burst and release their drug contents via said ends. As illusrated by device 110 in FIG. 11, it is of course not required tha both ends of such a device be exposed. In device 110, covered device 80 is affixed to a crossbar 111 to form a "T". Drug depots are present within device 80. The contents of these depots are released serially by bursting as uterine fluids enter the bottom end of the axial arm of device 110 and generate pressure within the depots. Devices 90 and 110 give a drug release which is continuous, prolonged, and at a substantially constant rate. Since the path over which the bursting fronts must travel is relatively long (the length of device 90, for example), a reasonably rapid (and thus less sensitive) rate of front travel may be employed, even over very extended periods of time such as a year or more. Thus, while intrauterine devices embodying the present invention may be used for relatively short term administration of drugs to the uterus, such as 0.5 to 7 days administration of an antibiotic or counterirritant, they may also be used for delivery of drugs to the uterus over extended periods of time such as several months. In this latter application, they find a preferred utility delivering progestational hormones, estrogenic hormones, and antifertility hormonal agents. These hormones are generally not water-soluble so, as noted above, it will generally be necessary to intimately add an osmotically effective solute to the hormone.

Devices 90 and 110 are just two of many possible shapes which the device of this invention might assume for use in the uterus. Other suitable shapes are catalogued in the text *Intrauterine Contraceptive Devices*, written by Shubeck, et al. and published in 1971 by Massachusetts Institute of Technology, which text is herein incorporated by reference.

Figure 8:
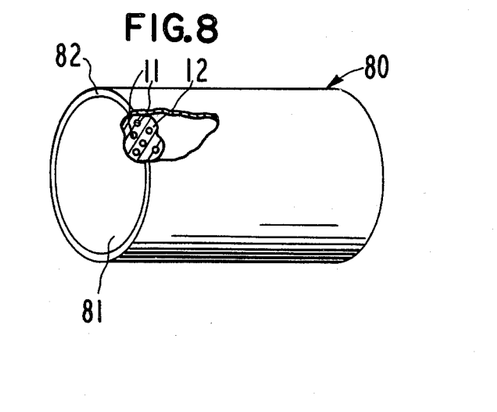
FIG. 8 is a partially cut-away perspective view of an enclosed tubular embodiment of the device of this invention.

In describing devices 80, 90 and 110, reference has been made to their water-impermeable outer walls or barrier membranes. Water permeability is a function of the permeability of the polymer forming the barrier and the thickness of the barrier. Good barrier membranes may be made from polymers that have a water permeability of less than $$10^{-10}(\text{gm·cm/cm}^2\text{·sec ·cm Hg})$$

provided the membrane is made sufficiently thick. Such polymers are polyethylene, polyvinylidene chloride, polyvinyl chloride, natural rubber, polyisoprene, polybutadiene, styrene/butadiene copolymers, ethylene/propylene rubbers and tetrafluroethylene polymers. These membranes or walls must be imperforate and thick enough to not be perforated by the bursting taking place within the device core.

Figure 12:
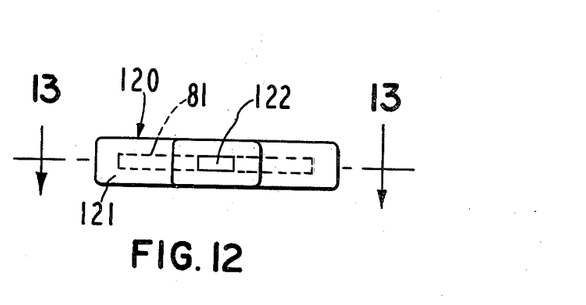
FIGS. 12 and 13 are elevational and cross-sectional views of a substantially enclosed embodiment of the invention.
Figure 13:
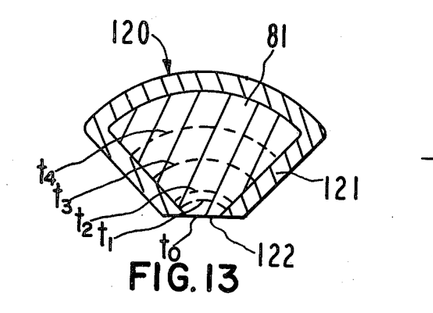

With the devices set forth in FIGS. 1–3 and 6–11, a decreasing or constant rate of drug release is obtained. FIGS. 12 and 13 illustrate a device, designated 120, that releases drug at an increasing rate. FIG. 12 is an elevational view of device 120, while FIG. 13 is a cross-sectional view of the same device. Device 120 contains a drug depot-containing polymer core 81 of essentially trapezoidal cross section. Device 120 contains a drug- and water-impermeable outer wall 121 which surrounds the top, bottom and all but one side of core 81. Core 81 is exposed at opening 122.

In use, body fluids initially contact core 81 at opening 122. Depot bursting initially occurs (at $t^0$) at this opening. The bursting front moves inward with time, respectively at sequential times $t_1$, $t_2$, $t_3$, and $t_4$, reaching the points in the core indicated by dotted lines in FIG. 13. The width of the bursting front increases as it moves inwardly. Since the front continues to move at a relatively constant rate, this means that increasing amounts of drugs are released and the rate of release increases.

EXAMPLES

The invention will be further described with reference to the following examples, which are intended to illustrate the invention and not to limit its scope. Unless indicated otherwise, parts are by weight. Release rates reported in these examples are expressed in terms of the rate of release of the free base form of the drug involved rather than the salt form. The values given for k are at ambient temperature.

EXAMPLE 1

A delivery device for the prolonged release of drug (pilocarpine nitrate) to the eye is prepared and tested in the following manner:

(b) Preparation of drug/polymer mixture.

A 7 grams portion of micronized pilocarpine nitrate is admixed with 3 grams of an ethylene-vinyl acetate copolymer (duPont ELVAX 40) containing about 40% vinyl acetate and having a melt index of 45–70 g/min (by ASTM D 1238 - modified test). This copolymer has a tensile strength of about 600–700 psi and an elongation at break of 1400% to 1500%. It is semi-permeable, being impermeable to pilocarpin nitrate but permeable to water. Pilocarpine nitrate is a water-soluble material, (about 25% solubility in water) and functions as an osmotically effective solute. The pilocarpin nitrate particles are on average ~40 microns in diameter. This mixture is heated to 120° C. and cast into a 0.6 mm thick film.

(b) Production of ocular inserts.

A number of 6 mm discs, suitable in size for installation in the sac of the eye, are cut from the 0.6 mm thick film. These discs have a surface area of 66 mm².

(c) Testing of inserts.

Figure 4:
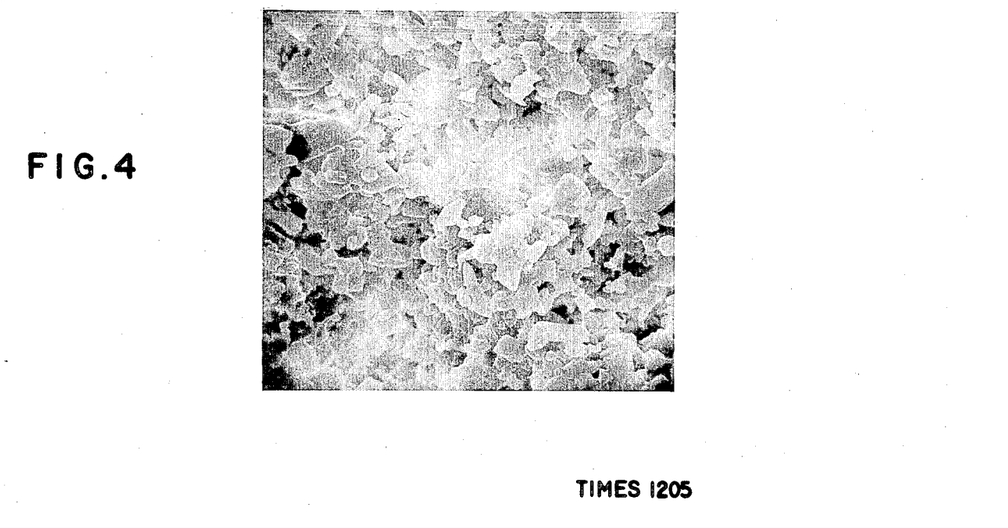
FIGS. 4 and 5 are scanning electron photomicrographs of the internal structure of a drug delivery device of this invention taken respectively before and after drug delivery is effected.
Figure 5:
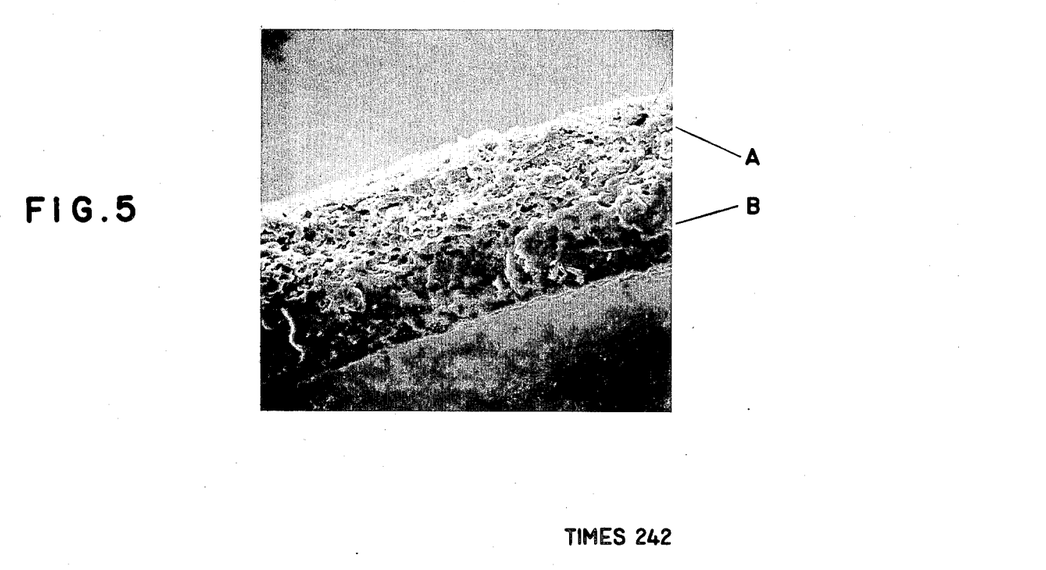

The inserts are placed in a simulated ocular aqueous environment. The outermost drug depots imbibe water, swell, and burst their enclosing membranes, releasing their drug and exposing innermore depots. The amount of drug released is monitored by an UV spectrometer set at 215 nanometer wavelength. A relatively rapid release of pilocarpine nitrate begins to be noticed. The release continues for about 22 hours at a rate gradually decreasing from an initial 400 microgram per hour to about 250 micrograms per hour after 22 hours. After 22 hours, the release rate falls rapidly. Microscopic and macroscopic comparison of the devices before and after use show that they retain their unit configuration but release drug by bursting the matrix surrounding the drug depots. FIGS. 4 and 5 are electrophotomicrographs of this drug-containing matrix taken before and after drug release respectively, which show the effect of the bursting release.

EXAMPLE 2

A partially enclosed ocular drug delivery device is prepared.

Figure 14:
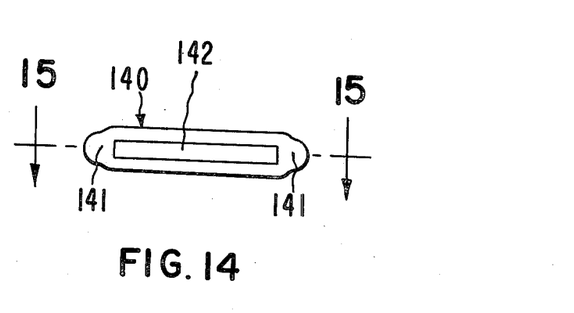
FIGS. 14 and 15 are elevational and cross-sectional views of another ocular delivery embodiment of this invention.
Figure 15:
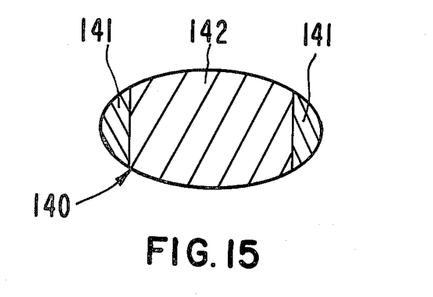

First a 100 mil wide by about 20 cm long strip is cut from the 0.6 mm thick pilocarpin nitrate-ethylene-vinyl acetate copolymer matrix prepared in Example 1. This strip is then laminated between two 0.08 mm sheets of water- and drug-impermeable clear polymeric material. Elliptical ocular inserts are punch cut from the laminate straddling the enclosed matrix. The inserts are on their axes 6 mm by 13 mm and have a 13 mm long, 2.5 mm wide and 0.6 mm thick strip of matrix running through their center. Only the 0.6×2.5 mm ends of the matrix are exposed. FIGS. 14 and 15 are elevational and cross-sectional views of such a device, designated 140, showing inner matrix 142 and outer laminate, partial covering 141.

One of these inserts is placed in a simulated ocular environment. Pilocarpine nitrate is released at a continuous controlled rate by the bursting mechanism described above. Visual examination of the devices proves that the bursting is taking place along a gradually migrating front, since the areas having drug present are an opaque white and the drug-exhausted matrix areas are translucent.

During the first two days, the release drops from about 75 micrograms/hour to about 50 micrograms/hour. For six additional days, the drug release rate is between about 50 and about 40 micrograms per hour. After about 200 hours of total test, the drug content is substantially exhausted and the drug release rate trails off to zero micrograms per hour.

EXAMPLES 3 THROUGH 5

To demonstrate the non-sensitivity to environmental conditions of the devices of this invention, one device as prepared in Example 2 is placed in an acidic (pH 4) aqueous environment, another is placed in an alkaline (pH 9) aqueous environment; and one is placed in a sample of aqueous laboratory waste. Even under these conditions, all devices continue to release drug substantially as described in Example 2.

EXAMPLES 6 AND 7

Twenty-five grams of progesterone (10μ particles) is mixed with 25 grams of sodium bicarbonate (10μ particles). The progesterone and NaHCO₃ are mixed together in a V-type drug blender for 24 hours. The drug/bicarbonate mixture is added to 50 g of Elvax 40 in a small enclosed mixer and mixed with heating for about 30 minutes. After mixing in the mixer, the intimately blended molten mass is extruded into a 3.8 mm ID polyethylene tube. A 3 cm length of this tube is sealed at one end and is heat bent into a loop configuration in accord with FIG. 9. A 2 cm length is employed as the center bar of a "T"-shaped device by being bonded to a solid polyethylene crossbar in accord with FIG. 10. When placed in human uteri, these devices each release progesterone at a rate of ~25 micrograms/day. The 3 cm long loop device maintains this rate of release for about four months; the "T" device for about two months. After these periods, the release rate falls.

EXAMPLE 8

Three grams of Elvax 40 is mixed with 27 grams tetrahydrofuran to yield a homogenous solution. Into this polymer solution is mixed 7 grams of triethylenethiophosphoramide (40μ sized particles). The drug/polymer/solvent mixture is cast and the solvent is driven off to yield 0.8 mm thick dry sheets. The polymer/drug sheets are cut into 2.4 mm wide strips which are subsequently laminated between two 0.1 mm thick sheets of drug- and water-impermeable polymeric material. Elliptical devices are punched from the laminate straddling the enclosed matrix. The devices, 13 mm long and 6 mm wide, have the 2.4 mm wide and 0.8 mm thick strip of matrix running through the center of the major axis. Only the ends of the matrix are exposed.

The device is implanted surgically directly at the site of the cancerous growth. As body fluids are imbibed by the exposed matrix, the device begins to release triethylenethiophosphoramide at a constant rate of about 2 milligrams/day. After 10 days, the drug will be depleted and the device may be removed.

EXAMPLE 9

The experiment of Example 1 is repeated with the change that instead of 7 grams of micronized pilocarpine nitrate, 7 grams of an intimate 50/50 mixture of hydrocortisone acetate and sodium chloride is employed.

The substantially insoluble hydrocortisone acetate alone would not promote sufficient water imbibition to effect bursting. In combination with the soluble salt, however, a bursting release is achieved.

EXAMPLE 10

(a) Preparation of drug/polymer mixture.

37.5 parts of the copolymer of Example 1 was dissolved in 150 parts methylene chloride. 12.5 parts tetracycline hydrochloride was mixed ultrasonically with 25 parts methylene chloride. The two mixtures were then combined and the vessels which contained them were rinsed with 10 parts methylene chloride, the rinse being added to the combined mixtures. The entire mixture was blended until the slurry had a smooth texture.

The slurry was cast and prepared into a 250–300 micron film.

(b) Production of ocular inserts.

A number of crescent-shaped (13.3 mm × 3.6 mm) inserts were punch cut from the above-described film, each of which contained 33.3 mg tetracycline hydrochloride.

A number of elliptical (5 mm × 8 mm) inserts were also punch cut from said film, each of which contained 2.40 mg tetracycline hydrochloride.

(c) Testing of inserts.

The crescent-shaped and elliptical inserts of part (b) were tested by the procedure described in Example 1, part c, with the UV monitoring at 356 nanometer wavelength.

The initial tetracycline hydrochloride release rate from the crescent-shaped inserts was found to be approximately 25 μg/hr. This rate had decreased to between 8–9 μg/hr after 40 hours and then generally leveled into a slowly decreasing curve. After 160 hours the release rate was 4 μg/hr.

The initial release rate from the elliptical inserts was approximately 17 μg/hr. This rate had decreased to about 8 μg/hr after 15 hours and thereafter leveled off in a slowly decreasing curve. After 160 hours, the release rate was about 2½ μg/hr.

The release mechanism was the same as that observed for the inserts of Example 1.

EXAMPLE 11

(a) Preparation of drug/polymer mixture.

A mixture of 85 parts of the polymer of Example 1 and 15 parts isoproterenol hydrochloride (particle size 5–100 microns) solvent case into a film. This film was placed in a shim and melt pressed at 50° C. into a 150 micron thick film.

A 150 micron thick film of a mixture of 70 parts of the polymer of Example 1 and 30 parts isoproterenol hydrochloride (particle size 5–100 microns) was prepared in a similar manner.

(b) Production of ocular inserts.

A number of 6 mm D circular discs were punch cut from the films described above. 450 micron thick laminates of these discs comprising a 70/30 polymer/isoproterenol hydrochloride disc sandwiched between two 85/15 polymer/isoproterenol hydrochloride discs were made by heat pressing the three discs together at 50° C.

(c) Testing of inserts.

The inserts of part (b) were tested by the procedure of Example 1, part (c), with the UV monitoring at 279 nanometer wavelength.

The initial release rate of isoproterenol hydrochloride was 30 μg/hr. This rate decreased rapidly during the first day of the test to about 7 μg/hr, at which it leveled off. After 120 hours, the release rate was still about 7 μg/hr.

The release mechanism was the same as that observed for the inserts of Example 1.

EXAMPLE 12

An ocular device for releasing pilocarpine nitrate to the eye was prepared and tested in the following manner.

(a) Preparation of drug/polymer mixture and ocular devices.

A 8.75 g portion of micronized pilocarpine nitrate ($\rho = 1.36$ g/cm³, $\pi = 37$ atm) was blended with 16.25 g ethylene-vinyl acetate copolymer (duPont ELVAX 210) having a vinyl acetate content of 28% and a melt index of approximately 400 (density = 0.94 g/cm³, $k = 1.9 \times 10^{-10}$ g cm/cm$^2$ sec cm Hg, $T_s = 300$ psi, $Y = 600$ psi). Blending was performed in a Brabender Plasticorder half-size internal mixer for 25 minutes at ambient temperature. The resulting blend was passed through the cooled rolls of a 3×8 inch rubber mill to form a rough 0.9 mm thick sheet. 12 g portions of the sheet were compression molded between heated plattens of a hydraulic press at 65° C. for 5 min. to form 0.5 mm thick films. The molded films were surface washed in distilled water and desiccator dried. The pilocarpine nitrate was separated from a sample of the film by dissolving off the polymer and its specific surface area was determined by the above mentioned techniques and the surface area average diameter, d, was calculated to be 1.5 microns.

Elliptical ocular devices having a surface area, A, of 1.2 cm$^2$ were punched from the dry films.

(b) Testing of Devices

The devices were placed in a simulated tear fluid environment and the amount of pilocarpine nitrate released was monitored by a UV spectrometer set at 215 nanometers wavelength. The devices initially released 100 mcg/hr. The rate gradually decreased to 45 mcg/hr at 30 hr and remained stable to 168 hr. After 170 hr, the rate dropped rapidly as the devices were exhausted of pilocarpine nitrate.

EXAMPLE 13

(a) Preparation of drug/polymer mixture and ocular devices 6 parts of the polymer of Example 12 was masticated on a roll mill until a film was formed. 4 parts of diethylcarbamazine citrate ($\rho = 1.3$ g/cm$^3$, $\pi = 108$ atm) was added slowly to the film during further mastication. The mixture was repassed through the mill to obtain a smooth dispersion of the diethylcarbamazine citrate in the polymer. The resulting sheet was placed in a shim and heat pressed at 65° C. for 5 min. into a 500 micron thick sheet. The surface area average diameter, d, of the diethylcarbamazine citrate was about 5 microns. Elliptical ocular devices 5.8 mm × 13.5 mm, A = 1.2 cm$^2$, were punch cut from the film.

(b) Testing of Devices

The devices of part (a) were tested by the procedure of Example 12, part (b) with the UV monitoring at 213.5 nm wavelength. The initial release of diethylcarbamazine citrate was about 30 mcg/hr. This rate leveled off after one day to about 25 mcg/hr and this rate held with a slight decrease for about 5 days. After 5 days the release rate decreased rapidly.

EXAMPLE 14

(a) Preparation of drug/polymer mixture and vaginal devices 20 g of sodium bicarbonate ($\rho = 2.16$ g/cm$^3$, $\pi = 240$ atm) were blended with 20 g of the sodium salt of candicidin. Both ingredients of the blend had a surface area average diameter, d of 10 microns. This blend was in turn blended on a rubber mill with 18 g of the copolymer of Example 12 and 42 g of ethylene-vinyl acetate copolymer (DuPont ELVAX 40) having a vinyl acetate content of 40 wt % (density = 0.96 g/cm$^3$, $k = 4.5 \times 10^{-10}$ g cm/cm$^2$ sec cmHg, $T_s = 650$ psi, $Y = 300$ psi). The resulting mixture was extruded into a 4 mm diameter rod. Devices 3 cm long were cut from the rod.

(b) Testing of Devices

The devices were placed in a simulated vaginal fluid environment and the amount of the sodium salt of candicidin released was monitored by a UV spectrometer set at 364 nanometers wavelength. After an initial, short priod of unsteady state release the release rate of candicidin-Na was substantially constant at 500 mcg/day-cm$^2$ for about 2 weeks.

EXAMPLE 15

(a) Preparation of drug/polymer mixture and ocular devices 24 g of epinephrine bitartrate ($\rho = 1.5$ g/cm$^3$, $\pi = 78$ atm) were blended with 76 g of the copolymer of Example 12 in an internal mixing bowl. The resultant blend was extruded into a 700 micron thick sheet. The epinephrine bitartrate was separated from a sample of the sheet and its specific surface area was measured by the above mentioned techniques. From this measurement the surface area average diameter of the epinephrine bitartrate particles in the sheet was calculated to be 5 microns. Elliptical ocular devices 10.6×3.8 mm were cut from the sheet.

(b) Testing of Devices

The devices of part (a) were tested by the procedure of Example 12, part (b), with UV monitoring at 279 nm wavelength. After an initial short period of unsteady state release the devices released the drug at a substantially constant rate of 6 mcg/hr for one week.

EXAMPLE 16

(a) Preparation of drug/polymer mixture and ocular devices 40 g of tetracycline hydrochloride ($\rho = 1.45$ g/cm$^3$, $\pi = 10.3$ atm) were blended with 60 g of the copolymer of Example 12. The resultant blend was extruded into a 700 micron thick sheet. The tetracycline hydrochloride was separated from a sample of the sheet and its specific surface area was measured by the above mentioned techniques. From this measurement the average diameter of the drug particles in the sheet was calculated to be 6.1 microns. Elliptical ocular devices 5×8 mm were cut from the sheet.

(b) Testing of Devices

The devices of part (a) were tested by the procedure of Example 12, part (b), with UV monitoring at 356 nm wavelength. After an initial short period of unsteady state release the devices released drug at a substantially constant rate of 30 mcg/hr for over one week.

EXAMPLE 17

The effect of the volume %, $\Phi$, of drug composition depots on the release rate of drug was illustrated by making two sets of devices identical in all respects except in the volume % of the depots. One set met relationship 1 above, the other did not.

Figure 16:
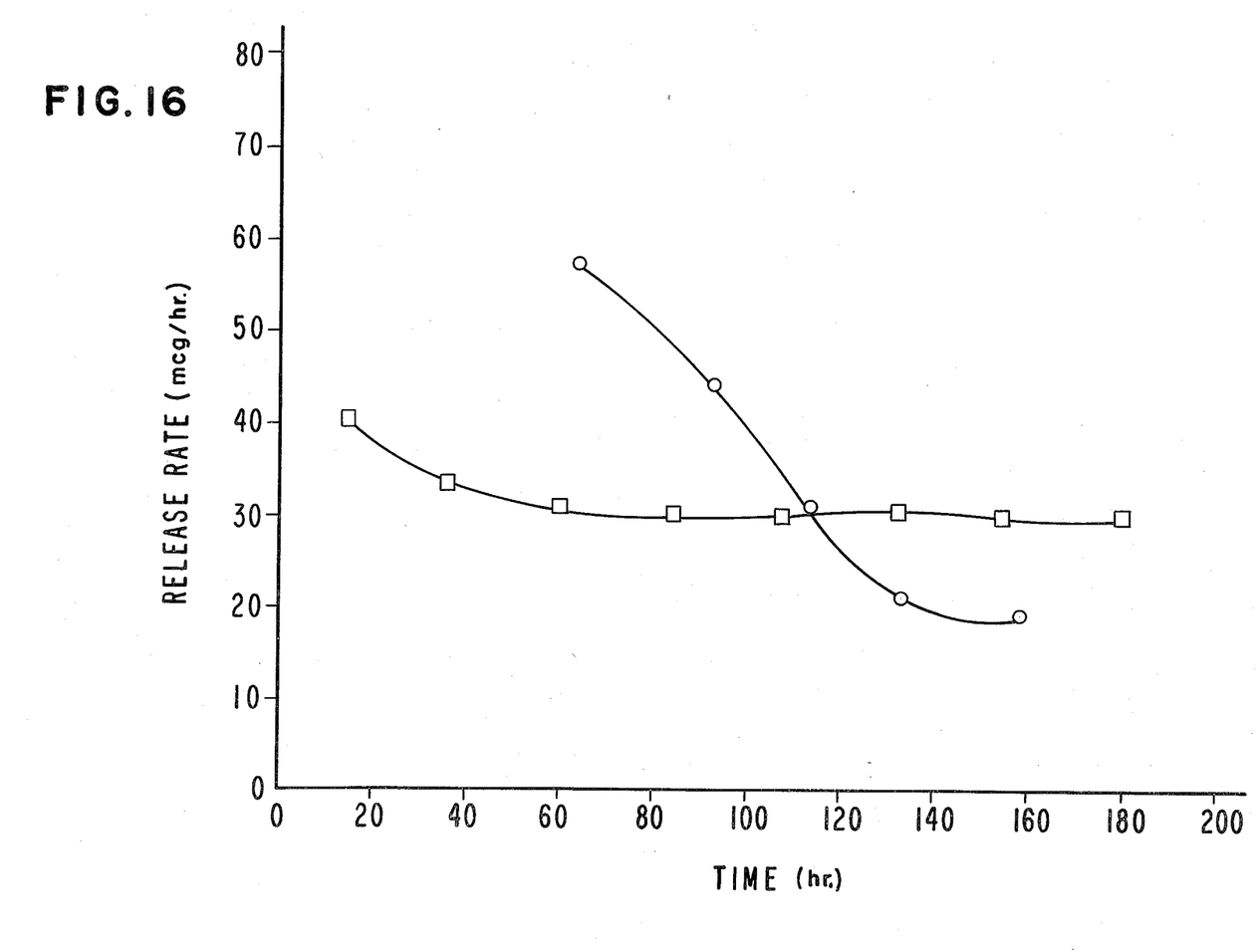
FIG. 16 is a graph showing the drug release rates of the devices of Example 17 as a function of the volume percent of drug in those devices.

The devices of both sets consisted of the copolymer of Example 12 and pilocarpine nitrate having a specific surface area of 1.3 m$^2$/g (d = 3.4 microns). In the set meeting relationship 1, the volume % of pilocarpine was 22.9, in the other it was 36.2. The release rates of pilocarpine nitrate from these devices were determined by the procedure of Example 12, part (b). These rates, in mcg/hr, are plotted against time in FIG. 16, with the squares representing data for the devices meeting relationship 1 and the circles representing data for the other set. As shown in FIG. 16 after an initial 22 hr period of nonsteady state release the devices meeting relationship 1 exhibited an essentially constant release rate of approximately 30 mcg/hr. The other devices exhibited a release rate approximately proportional to time$^{-\frac{1}{2}}$.

EXAMPLE 18

The effect of depot size, d, on the release rate of drug was illustrated by making two sets of devices identical in all respects except in depot size. One set met relationship 1 above, the other did not.

Figure 17:
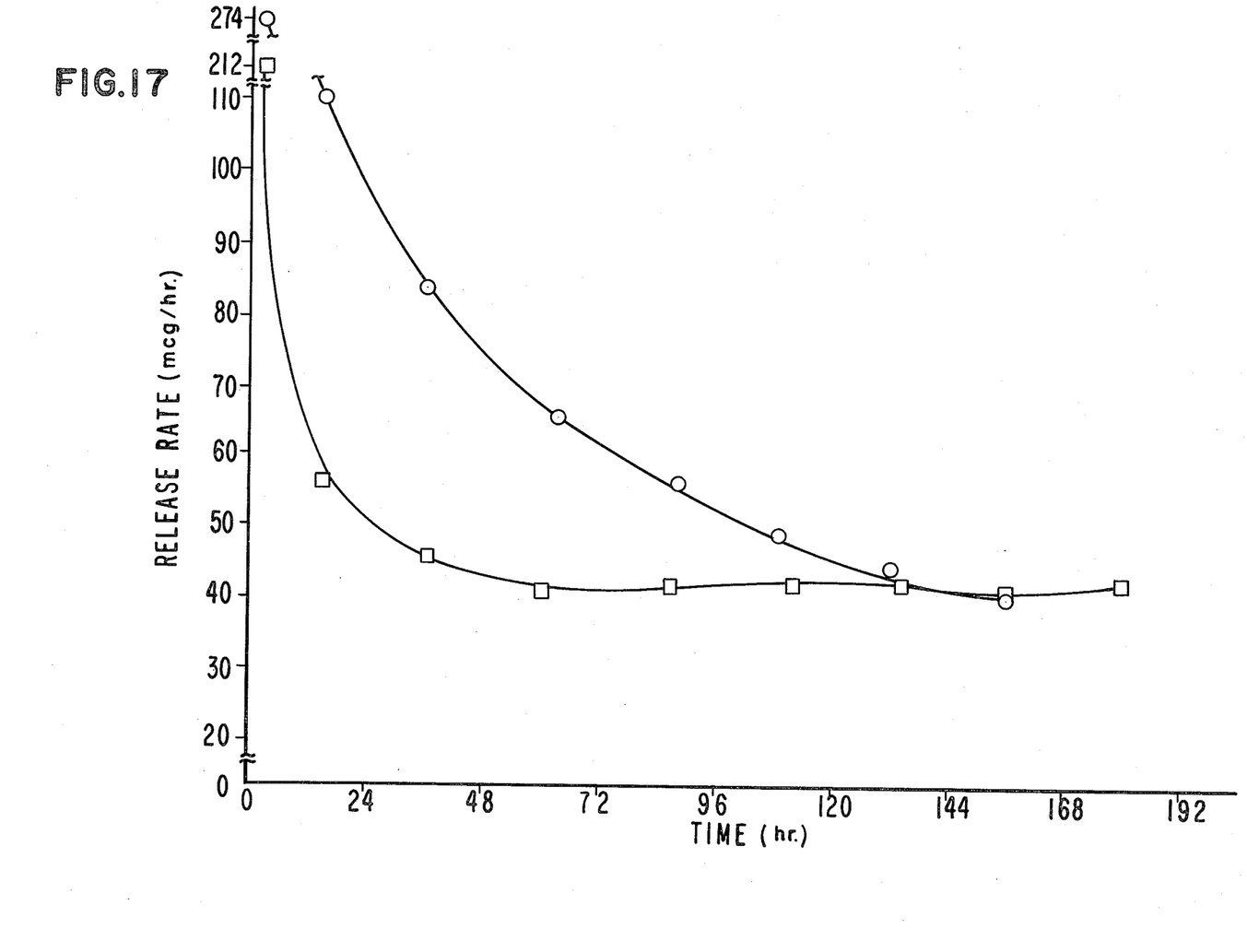
FIG. 17 is a graph showing the drug release rates of the devices of Example 18 as a function of the surface area average diameter of the drug composition depots of those devices.

The devices of both sets consisted of 73 v% of the copolymer of Example 12 and 27 v% pilocarpine nitrate. In the one meeting relationship 1 the pilocarpine nitrate had a specific surface area of 1.3 m²/g (d=3.4 microns). In the other the pilocarpine nitrate had a specific surface area of 3.6 m²/g (d=1.2 microns). The release rates of pilocarpine nitrate from these devices were determined by the procedure of Example 12, part (b). These rates, in mcg/hr, are plotted against time in hr in FIG. 17, with the squares representing data for the set meeting relationship 1 and the circles representing data for the other set. As shown in FIG. 17 after an initial 24 hr period of nonsteady state, high pilocarpine nitrate release the devices meeting relationship 1 exhibited an essentially constant release rate of approximately 40 mcg/hr. In contrast the other set of devices exhibited a release rate approximately proportional to time$^{-\frac{1}{2}}$.

Modifications of the above described osmotic bursting drug delivery devices that are obvious to those of skill in the chemical, polymer, pharmaceutical, or medical arts are intended to be within the scope of the following claims.

We claim:

1. A drug delivery device for administering drug continuously to an aqueous body environment for a prolonged time period at a controlled rate, said device being in the form of a solid, unit body that:
   (a) is sized and shaped for placement in the environment; and
   (b) consists essentially of a mixture that defines a surface of predetermined area that is exposed to the water in said environment, said mixture consisting essentially of
   (i) about 1% to about 50% by volume, of discrete depots 0.1 to 250 microns, surface area average diameter, in size of a drug composition that is an osmotically effective solute, said depots being dispered in
   (ii) about 50% to about 99%, by volume, of a polymer such that the depots are surrounded substantially individually by a layer of the polymer, the polymer being substantially impermeable to the drug composition, insoluble in the environment at least during the prolonged time period, and permeable to water and having a tensile strength, Young's modulus, and a maximum elongation such that the cohesive strength of said layer is exceeded by the pressure that the depot the layer surrounds is able to generate by imbibing water, whereby when the device is placed in the environment, water is imbibed by the depots in a serially inwardly manner beginning with the depots nearest said surface and said pressure is generated therein, causing the polymer layers surrounding said depots to rupture thereby releasing drug composition therefrom to the environment.

2. The drug delivery device of claim 1 wherein the drug composition consists essentially of a drug that is itself an osmotically effective solute.

3. The drug delivery device of claim 1 wherein the drug composition consists essentially of a drug that is not an osmotically effective solute mixed with a compound that is an osmotically effective solute.

4. The drug delivery device of claim 1 wherein the unit body is made entirely of said mixture.

5. A drug delivery device for releasing drug continuously to an aqueous body environment for a prolonged time period at a controlled rate said device being in the form of a solid unit body that is sized and shaped for placement in the environment and consists essentially of a mixture of (i) about 1% to about 50% by volume of a drug composition that when in aqueous solution exhibits an osmotic pressure of at least about 10 atmospheres and that is in the form of discrete depots having a surface area average diameter, d, of about 0.1 to about 250 microns, wth the proviso that:

$$d \geq \frac{0.5}{\left(\frac{\pi}{.06\Phi}\right)^{\frac{1}{2}} - 1}$$

wherein $\Phi$ is the volume percent of drug composition in the mixture and (ii) about 50% to about 99% by volume of a polymer that has a permeability to water of about $10^{-8}$ to about $10^{-12}$ g cm/cm² sec cm Hg, a tensile strength of about 200 to about 3000 psi, a Young's modulus of about 200 to about 3000 psi and is substantially impermeable to the drug composition and insoluable in the environment at least during the prolonged time period; the depots being dispersed in the polymer such that the depots are surrounded substantially individually by the polymer.

6. A drug delivery device for releasing drug continuously to an aqueous body environment for a prolonged time period at a substantially constant rate, said device:
   (a) being in the form of a solid unit body that is sized and shaped for placement in the environment;
   (b) having a surface of predetermined area, A, that is exposed to the water in said environment when the device is placed therein; and
   (c) consisting essentially of a mixture of
   (i) about 1% to about 35% by volume of drug composition that when in aqueous solution exhibits an osmotic pressure of at least about 10 atm, has a density, $\rho$, of about 0.5 to about 8 g/cm³, and is in the form of discrete depots having a surface area average diameter, d, of about 0.1 to about 250 microns, and an average depot-to-depot separation in the mixture of at least about 0.5 microns, with the proviso that $$d \geq \frac{0.5}{\left(\frac{\pi}{.06\Phi}\right)^{\frac{1}{2}} - 1}$$

where $\Phi$ is the volume percent of drug composition in the mixture, and
   (ii) about 65% to about 99% by volume of a polymer that has a permeability to water, k, of about $10^{-8}$ to about $10^{-12}$ g cm/cm² sec cm Hg, a tensile strength, $T_s$, of about 200 to about 3000 psi, and a Young's modulus, Y, of about 200 to about 3000 psi and is substantially impermeable to the drug composition and insoluble in the environment at least during the prolonged time period, and, said rate is proportional to $$\frac{\rho \Phi \times 10^{-2} k \Delta\pi A}{d(\lambda^3 - 1)\left[1 - \left(\frac{.06\Phi}{\pi}\right)\right]^{\frac{1}{2}}}$$

where $\rho$, $\Phi$, k, A, and d are as defined previously, $\Delta\pi$ is the difference between the osmotic pressures of the drug composition in aqueous solution and the environment, and $$\lambda^2 - \lambda^{-4} = 3T_s/Y$$

wherein $T_s$ and Y are as defined previously, with the proviso that $\lambda$ is in the range of 1.02 and 4.0, said depots being dispersed in said polymer such that said depots are encapsulated and surrounded substantially individually by a layer of said polymer.

7. The drug delivery device of claim 6 wherein said average diameter is 1 to 50 microns, said permeability to water is $10^{-9}$ to $10^{-10}$ g cm/cm$^2$ sec cm Hg, said tensile strength is 400 to 1500 psi, said Young's modulus is 300 to 1500 psi, and the polymer has a maximum elongation of 2000% to 1700%.

8. The drug delivery device of claim 7 wherein the polymer is an ethylene-vinyl acetate copolymer.

9. The drug delivery device of claim 8 wherein the environment is a cul-de-sac of the eye.

10. The drug delivery device of claim 9 wherein the drug is pilocarpine nitrate, diethylcarbamazine citrate, epinephrine bitartrate, or tetracycline hydrochloride.

11. The drug delivery device of claim 6 wherein the device consists entirely of said mixture.

12. The drug delivery device of claim 1 wherein said environment is a cul-de-sac of the eye.

* * * * *